US00PP09817P

United States Patent [19]

VandenBerg

[11] Patent Number: Plant 9,817

[45] Date of Patent: Mar. 4, 1997

[54] CHRYSANTHEMUM PLANT NAMED 'JANICE'

[75] Inventor: Cornelis P. VandenBerg, Salinas, Calif.

[73] Assignee: Yoder Brothers, Inc., Barberton, Ohio

[21] Appl. No.: 609,491

[22] Filed: Mar. 1, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 6,621 2/1989 Mack et al. ..... Plt./78

P.P. 7,725 11/1991 Fuess ..... Plt./78

*Primary Examiner*—Howard J. Locker

*Attorney, Agent, or Firm*—Foley & Lardner

[57] ABSTRACT

A Chrysanthemum plant named Janice particularly characterized by its flat capitulum form; decorative capitulum type; yellow ray floret color; diameter across face of capitulum of 38 to 44 mm when fully opened; branching pattern is spreading and prolific, with 7 to 9 laterals developing after pinch when grown outside under natural daylength in fall flowerings; natural season flower date of August 13 to 16 when planting rooted cuttings on June 17 to 18 in Salinas, Calif, and of September 12 to 18 when planting rooted cuttings June 15 to 18 in Highstown, N.J.; plant height of 25 to 30 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Janice.

Janice, identified as 8017 (92-668001), was originated from an open pollination program, where the best breeding lines were selected by Cornelis P. VandenBerg, flowered under controlled conditions outdoors and left to be pollinated by bees, in Salinas, Calif., in September of 1991.

The female parent of Janice was the cultivar identified as Holly, disclosed in U.S. Plant Pat. No. 7,992, and described as garden mum with yellow flower color.

The male parent of Janice is unknown, since the female parent of Janice was open pollinated.

Janice was discovered and selected as one flowering plant within the progeny of the stated cross by Cornelis P. VandenBerg in October of 1992 in a controlled environment in Salinas, Calif.

The first act of asexual reproduction of Janice was accomplished when vegetative cuttings were taken from the initial selection in December of 1992 in a controlled environment in Salinas, Calif., by technicians working under the supervision of Cornelis P. VandenBerg.

Horticultural examination of controlled flowerings of successive plantings has shown that the unique combination of characteristics as herein disclosed for Janice are firmly fixed and are retained through successive generations of asexual reproduction.

Janice has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Janice, which, in combination, distinguish this Chrysanthemum as a new and distinct cultivar:

1. Flat capitulum form.
2. Decorative capitulum type.
3. Yellow ray floret color.

4. Diameter across face of capitulum of 38 to 44 mm when fully opened.
5. Branching pattern is spreading and prolific, with 7 to 9 laterals developing after pinch when grown outside under natural daylength in fall flowerings.
6. Natural season flower date of August 13 to 16 when planting rooted cuttings on June 17 to 18 in Salinas, Calif., and of September 12 to 18 when planting rooted cuttings June 15 to 18 in Highstown, N.J.
7. Plant height of 25 to 30 cm when grown in fall under natural daylength with no growth regulators.
8. Durable, uniform performance.

The accompanying photographic drawings show typical inflorescence and leaf characteristics of Janice, with the colors being as nearly true as possible with illustrations of this type.

Sheet 1 is a color photograph of Janice grown in natural season outside conditions in Salinas, Calif.

Sheet 2 is a black and white photograph of three views of the inflorescence of Janice.

Sheet 3 is a black and white photograph showing the upper and under sides of the leaves of Janice at 3 stages of development (mature, intermediate and immature).

In sheets 2 and 3 a measuring tape in centimeters has been added.

Of the commercial cultivars known to the inventor, the most similar in comparison to Janice is the cultivar identified as Jessica, disclosed in U.S. Plant Pat. No. 7,587. Reference is made to attached Chart A, which compares certain characteristics of Janice to the same characteristics of Jessica.

Similar traits are capitulum form and type, and branching pattern. The ray floret color of Janice (R.H.S. 12A) is a more golden yellow that the ray floret color of Jessica (R.H.S. 6A to 9A). Janice has a slightly smaller diameter of capitulum, a slower natural season flowering response in New Jersey, and a shorter plant height when compared with Jessica. The natural season flowering response in California is comparable for both cultivars.

In the following description color references are made to The Royal Horticultural Society Colour Chart. The color values were determined on plant material grown as a pinched garden mum grown outdoors in Salinas, Calif. on Aug. 18, 1995.

Classification:

*Botanical.*—*Dendrathema grandiflora* cv Janice.

*Commercial.*—Flat decorative garden mum.

INFLORESCENCE

A. Capitulum:

*Form.*—Flat.

*Type.*—Decorative.

*Diameter across face.*—38 to 44 mm when fully opened.

B. Corolla of ray florets:

*Color (general tonality from a distance of three meters).*—Yellow.

*Color (upper surface).*—12A.

*Color (under surface).*—12B.

*Shape.*—Straight, flat, rounded ray floret tips.

C. Corolla of disc florets:

*Color (mature).*—14B.

*Color (immature).*—14B, overlaid with 144B.

D. Reproductive organs:

*Androecium.*—Present on disc florets only; scant pollen.

*Gynoecium.*—Present on both ray and disc florets.

PLANT

A. General appearance:

*Height.*—25 to 30 cm when grown in fall under natural daylength with no growth regulators.

*Branching pattern.*—Spreading and prolific.

B. Foliage:

*Color (upper surface).*—147A.

*Color (under surface).*—147B.

*Shape.*—Small, lobed and slightly serrated.

CHART A

| CULTIVAR | JANICE | JESSICA |
|---|---|---|
| Ray floret color | Yellow | Yellow |
| Capitulum form and type | Flat decorative | Flat decorative |
| Diameter across face | 38 to 44 mm | 44 to 50 mm |
| Branching pattern | Spreading | Spreading |
| Nat. season flower date: | | |
| in Salinas, CA | Aug 13 to 16 | Aug 8 to 22 |
| in Hightstown, NJ | Sep 12 to 18 | Sep 8 to 14 |
| Plant height | 25 to 30 cm | 30 to 35 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

What is claimed is:

1. A new and distinct Chrysanthemum plant named Janice, as described and illustrated.

* * * * *

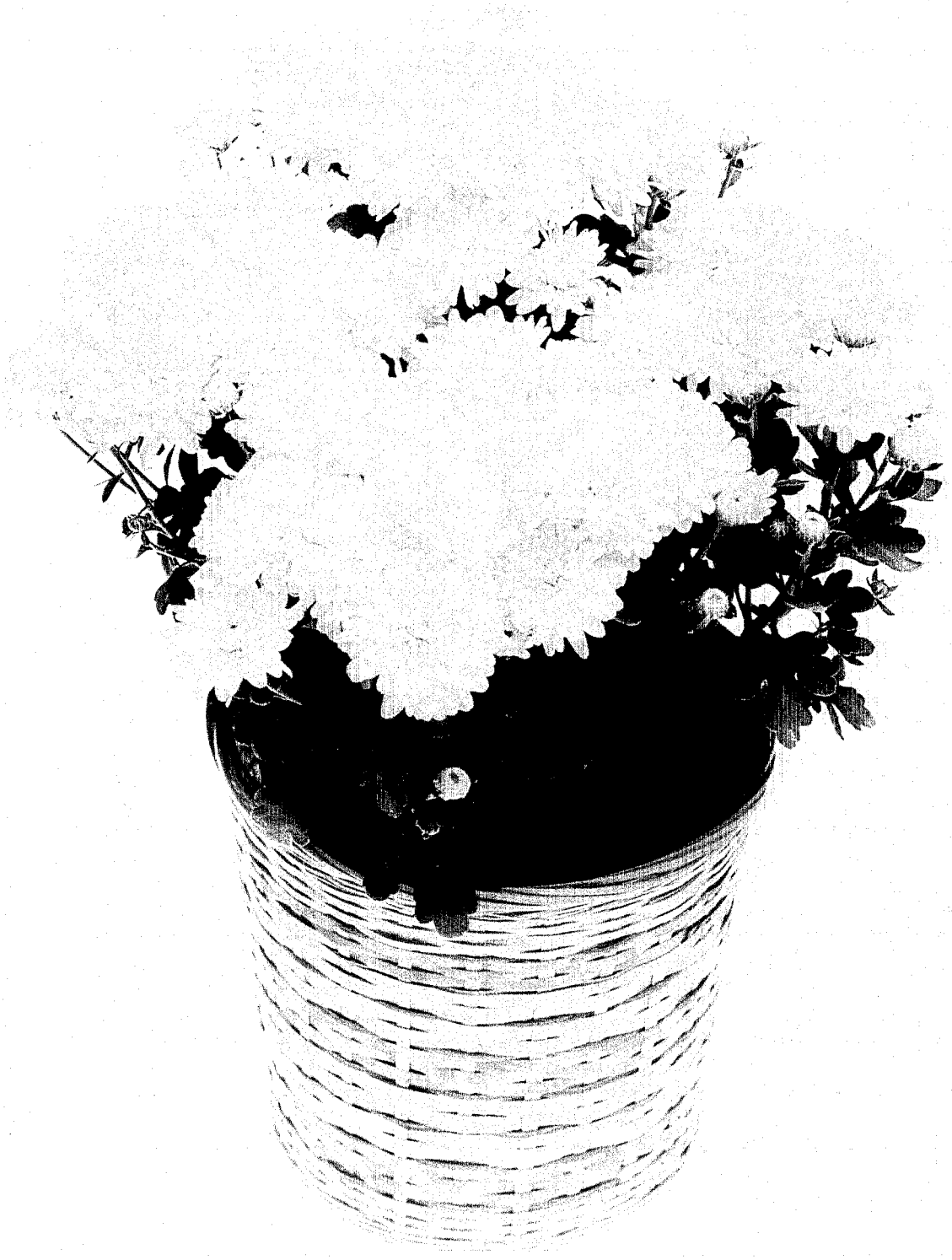

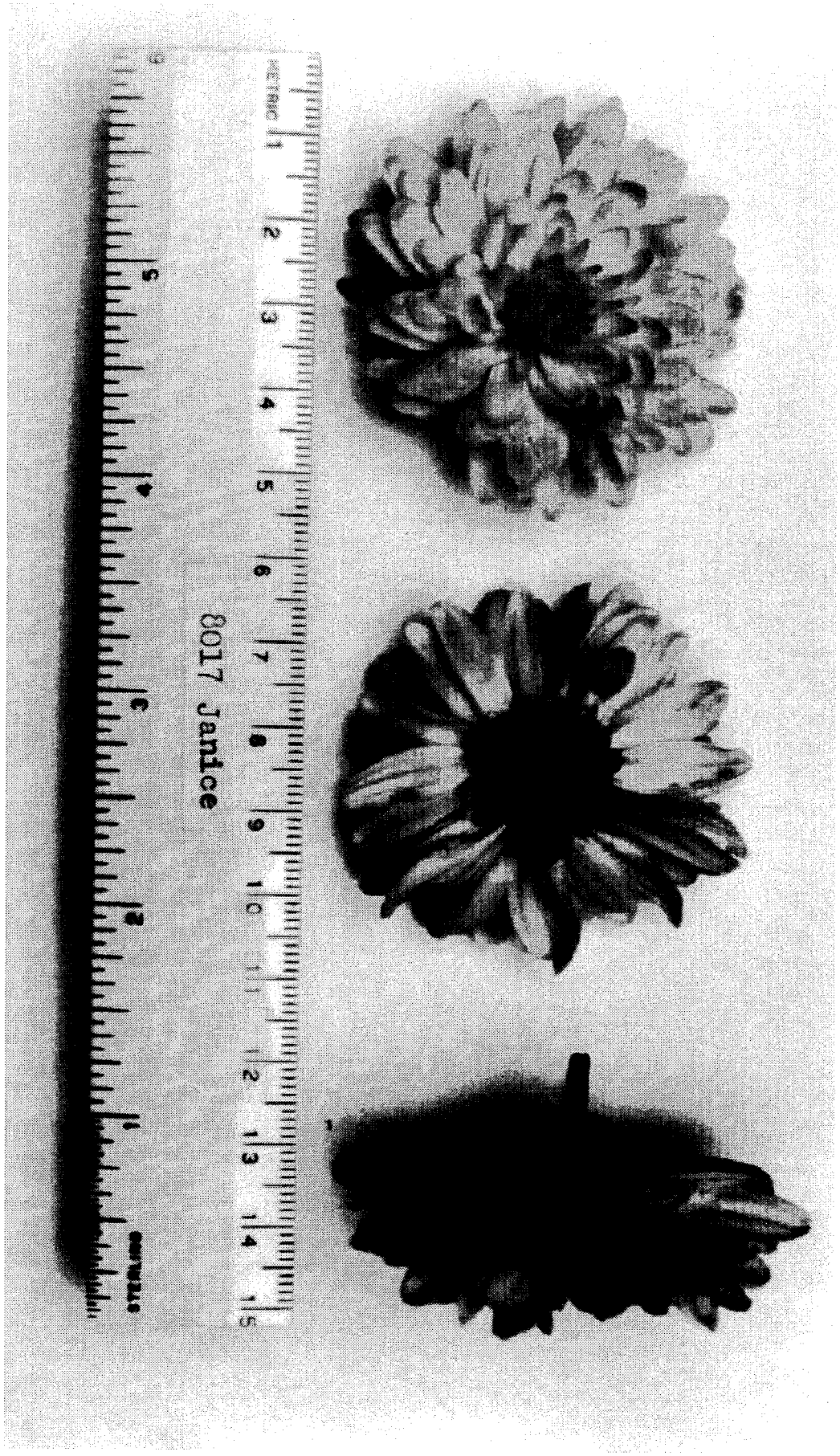
8017 Janice

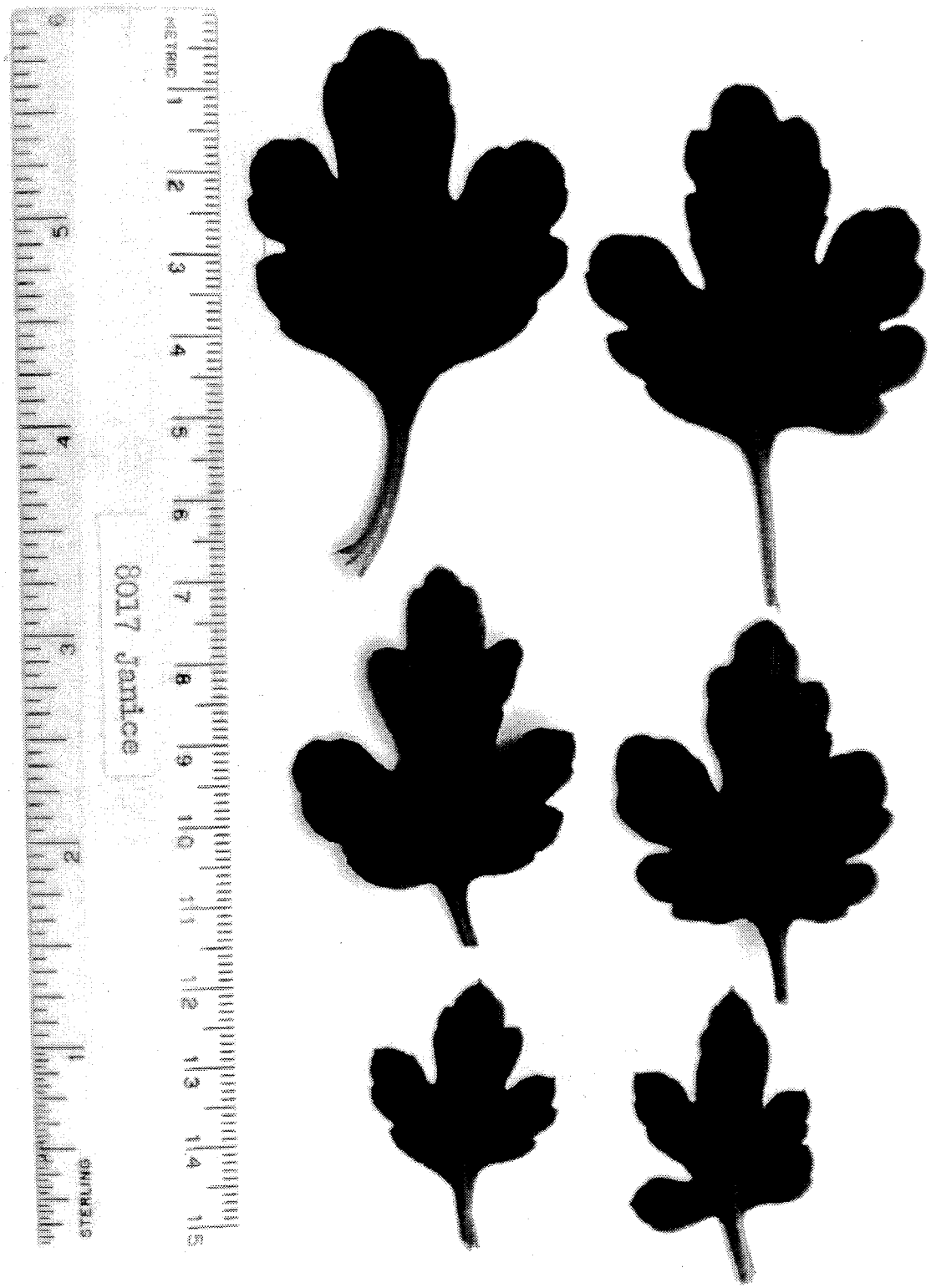
8017 Tantice